United States Patent [19]

Satake et al.

[11] Patent Number: 5,424,788
[45] Date of Patent: Jun. 13, 1995

[54] SLIT LAMP MICROSCOPE

[75] Inventors: Eiji Satake, Machida; Haruo Oda, Yokohama; Ken Tomioka, Zushi, all of Japan

[73] Assignee: Nikon Corporation, Tokyo, Japan

[21] Appl. No.: 874,705

[22] Filed: Apr. 28, 1992

[30] Foreign Application Priority Data

May 10, 1991 [JP] Japan ................................ 3-0105812

[51] Int. Cl.⁶ ............................................. A61B 3/10
[52] U.S. Cl. .................................. 351/206; 351/214; 354/62
[58] Field of Search ..................... 351/206, 214, 221; 354/62, 79

[56] References Cited

U.S. PATENT DOCUMENTS

| | | | |
|---|---|---|---|
| 3,614,214 | 10/1971 | Cornsweet et al. | 351/214 |
| 4,019,813 | 4/1977 | Cornsweet et al. | 351/214 |
| 4,773,749 | 9/1988 | Ohtomo et al. | 351/206 |
| 4,786,162 | 11/1988 | Fujiwara et al. | 351/206 |
| 4,807,989 | 2/1989 | Nagano et al. | 351/206 |
| 4,834,526 | 5/1989 | Nunokawa | 351/206 |
| 5,118,179 | 6/1992 | Sano et al. | 351/206 |

Primary Examiner—Ricky D. Shafer
Attorney, Agent, or Firm—Shapiro and Shapiro

[57] ABSTRACT

A slit lamp microscope is of the type having an illumination optical system for illuminating the eye to be examined, an observation optical system for observing the illuminated eye to be examined and a photographing unit. The slit lamp microscope comprises exposure control unit for controlling exposure at the time of photographing, a photographing conditions designation arrangement for designating at the time of photographing at least the designation of a part to the eye to be photographed and conditions regarding system of photographing, and an optimal exposure calculation unit for calculating an optimal exposure in accordance with the designated photographing conditions. The exposure control apparatus controls the exposure in accordance with the value of exposure calculated by the optimal exposure calculation unit when the photographing conditions are designated by the photographing conditions designation means.

11 Claims, 3 Drawing Sheets

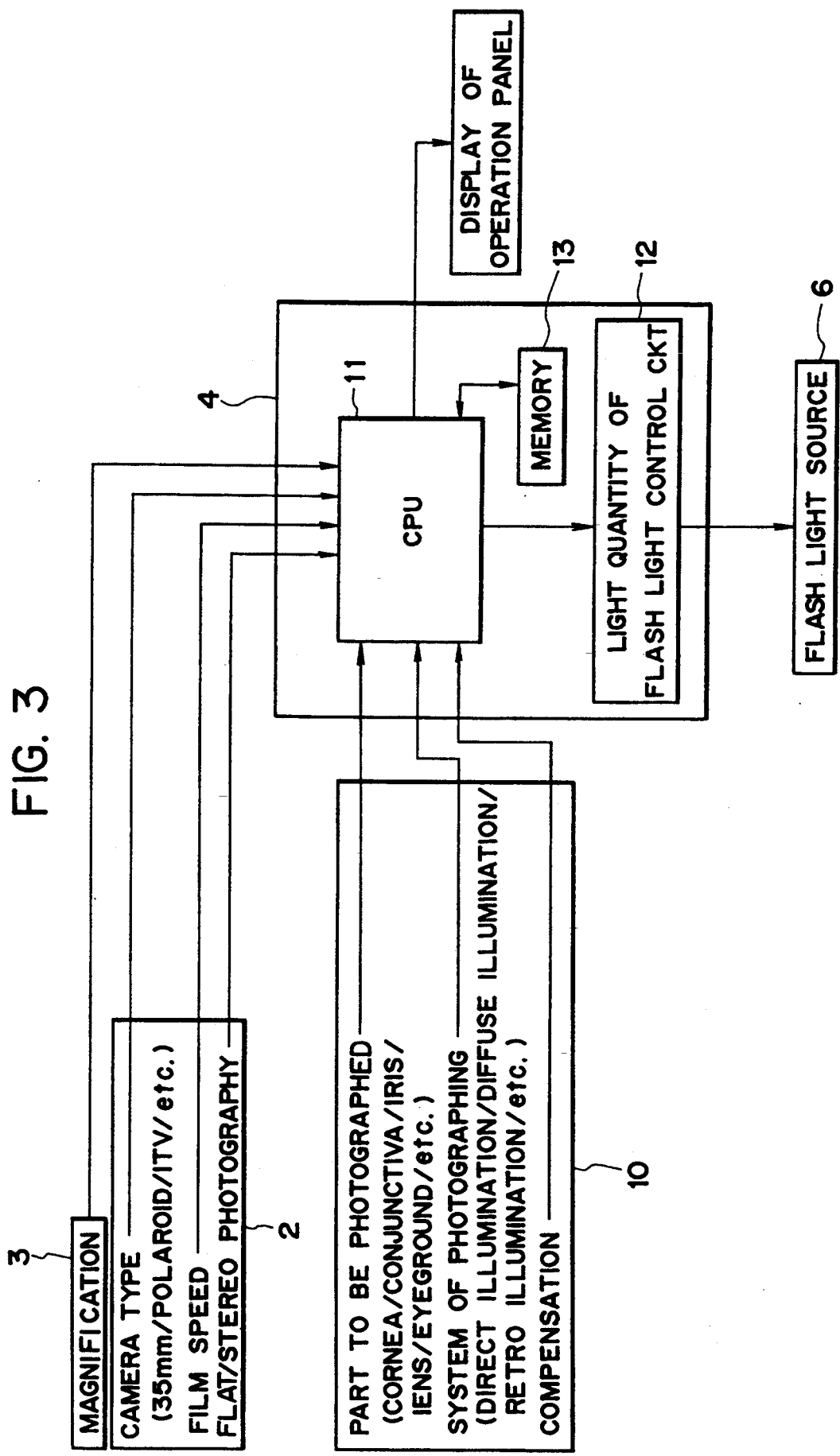

SLIT LAMP MICROSCOPE

BACKGROUND OF THE INVENTION

1. Field of the Invention

The present invention relates to a slit lamp microscope with an optimal exposure controlling apparatus.

2. Related Background Art

A slit lamp microscope is a kind of ophthalmologic device which is employed by those who are engaged in medical care such as an ophthalmologist for observing eyes to be examined. Photographing of an observed image by the slit lamp microscope is performed with a photographing apparatus mounted halfway in the observation optical path thereby to conduct the observing rays of light to the image taking plane. When photographing is performed by the slit lamp microscope, an optimal exposure differs in accordance with photographing conditions such as a part to be photographed, slit width, photographing magnification, camera type, and film speed. It is therefore necessary for a photographer to set an optimal exposure taking these conditions into account.

According to the conventional technique, it is required to consider the part to be photographed, slit width, photographing magnification, camera type, film speed etc. for setting the photographing conditions. Considerable skill is needed to decide the conditions appropriately in a short period without keeping the patient waiting, because there are various combinations of photographing conditions concerned.

SUMMARY OF THE INVENTION

It is an object of the present invention to provide a slit lamp microscope capable of deciding optimal exposure with ease by setting a part to be photographed and system of photographing in accordance with predetermined combinations.

According to the invention, there is provided a slit lamp microscope having an illumination optical system for illuminating the eye to be examined, an observation optical system for observing the illuminated eye to be examined, and a photographing unit, the slit lamp microscope comprising:

exposure control means for controlling exposure at the time of photographing;

photographing conditions designation means for designating at the time of photographing at least one of a part of the eye to be photographed and conditions regarding system of photographing;

optimal exposure calculation means for calculating an optimal exposure in accordance with the designated photographing conditions;

wherein the exposure control means controls the exposure in accordance with the value of exposure calculated by the optimal exposure calculation means when the photographing conditions are designated by the photographing conditions designation means.

It may be possible to provide the slit lamp microscope further with designation reception means for displaying at least either one of information indicating a photographing part of the eye to be examined, information regarding the system of photographing, and information indicating the combinations thereof for the reception of the designation of the displayed information.

With the photographing conditions designation means, the part to be photographed is set, and while fine adjustments are being made for difference in the appropriate amounts of light for each of the parts, the system of photographing is also defined. It is therefore possible to anticipate a typical slit width in that particular photography. Thus, without detecting the slit width, an optimal amount of light can be obtained with respect to the anticipated slit width.

BRIEF DESCRIPTION OF THE DRAWINGS

FIG. 3 is a block diagram showing an exposure control system.

DETAILED DESCRIPTION OF THE PREFERRED EMBODIMENT

Hereinafter, with reference to the accompanying drawings the description will be made for an embodiment according to the present invention.

Figure 1:
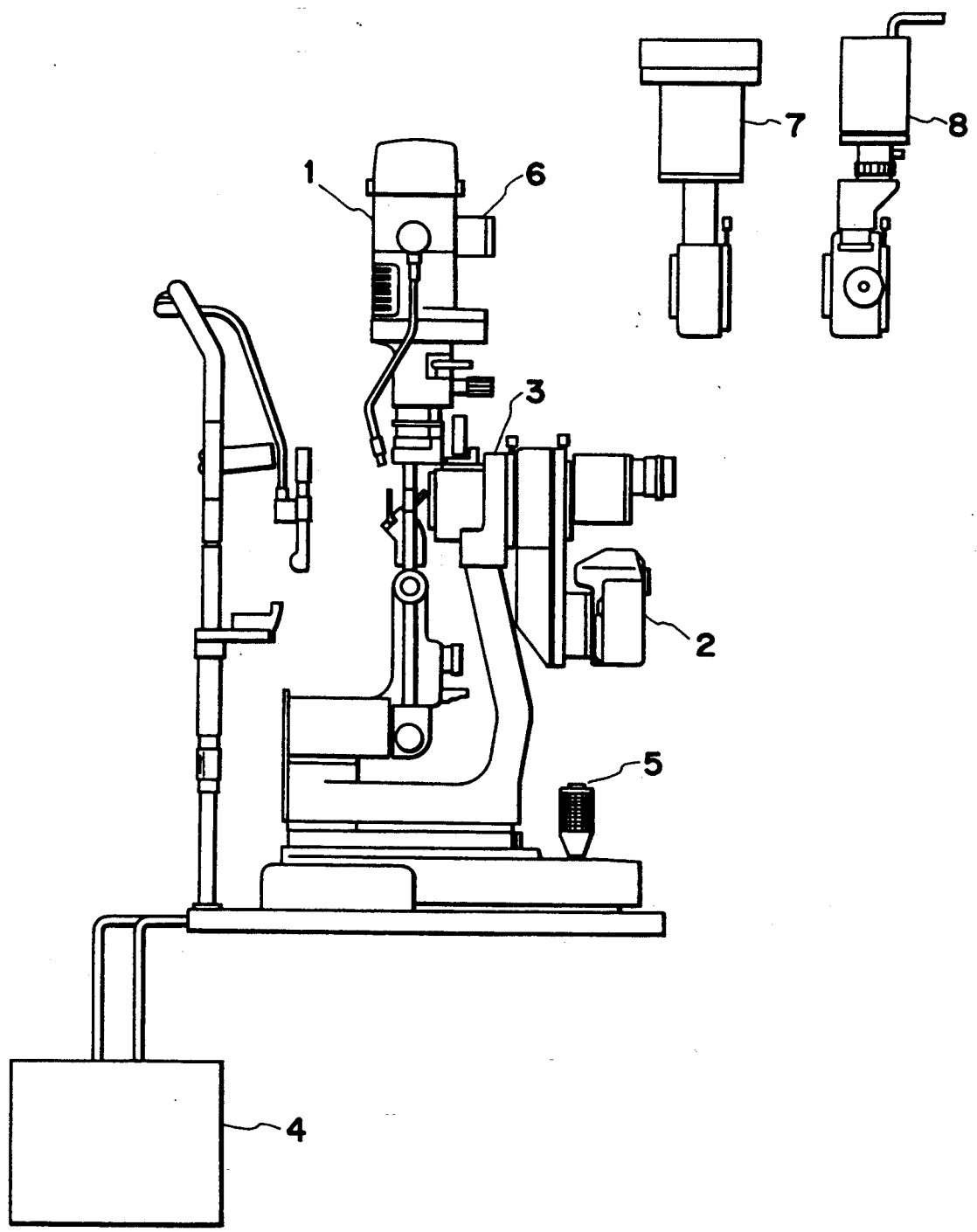
FIG. 1 is a view schematically illustrating a slit lamp microscope according to the present invention.

In FIG. 1, a reference numeral 1 designates a slit lamp illumination unit; 2, a 35 mm photographing (or camera) unit; 3, a variable power mechanism; 4 a program exposure control apparatus; 5, a release switch; 6, a flash light source; 7, an instant camera; and 8, an electronic still camera, respectively.

The 35 mm photographing unit 2 is provided with a mechanism for reading a DX code which indicates the speed of a film to be loaded. The variable power mechanism 3 includes a sensor for detecting magnification.

Figure 2:
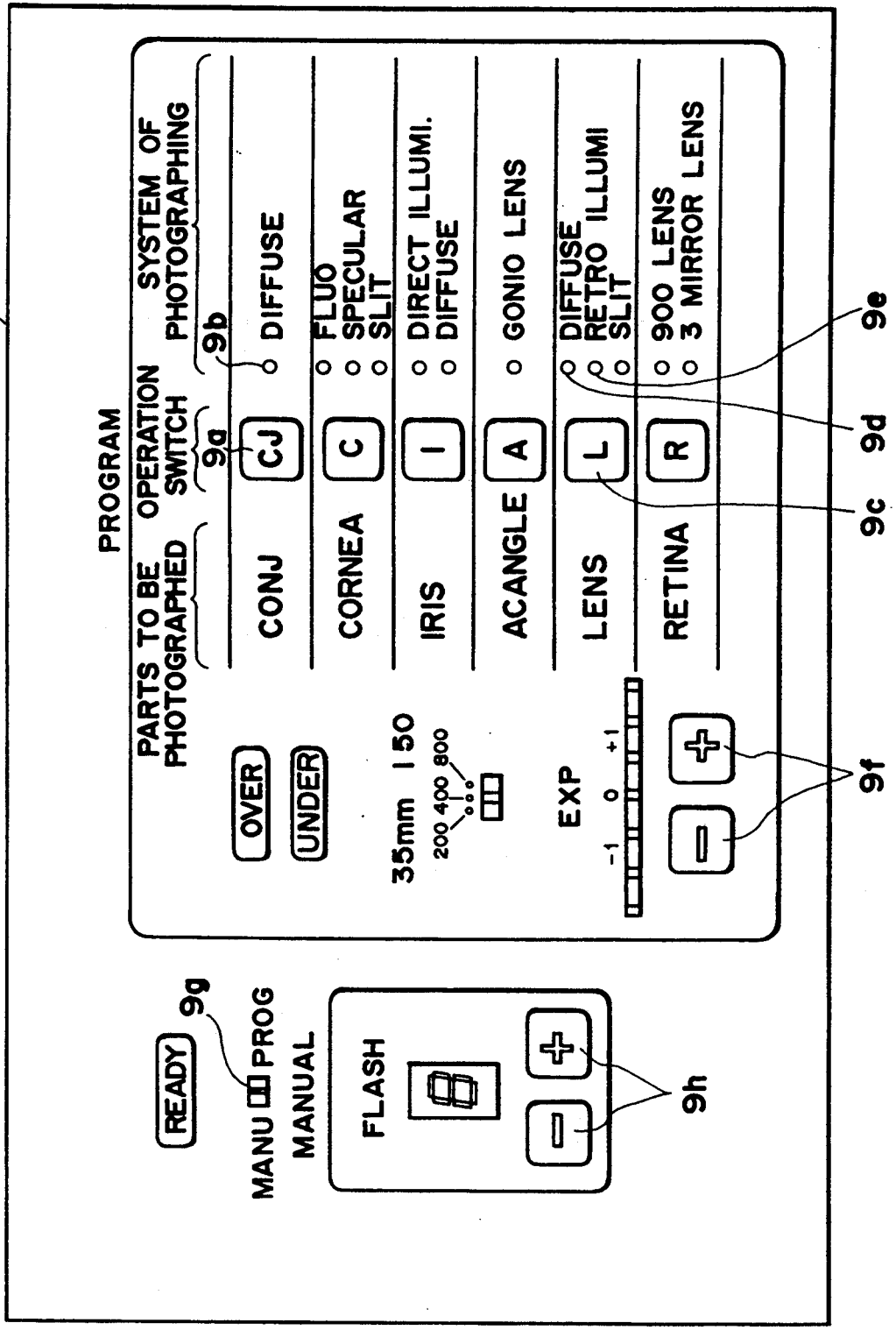
FIG. 2 is a view showing the operation panel for an exposure control apparatus.

FIG. 2 illustrates an example of an operation panel 10 arranged on the program exposure control apparatus 4 for setting a part to be photographed and system of photographing. For example, when a conjunctiva is photographed, the switch 9a which is marked CJ is depressed. Then, a light emitting diode (LED) 9b illuminates to indicate a photographing system using a diffuse illumination (DIFFUSE). Also, if a lens of the eye is photographed with a retro illumination, the switch 9c which is marked L is depressed twice. Then, an LED 9d illuminates for the first time, and an LED 9e, for the second time to indicate that the lens is photographed by the retro illumination. Likewise, by operation as set forth above, the other switches can be selected for the parts to be photographed and systems of photographing indicated on the operation panel.

If a compensation is desired for an exposure depending on the state of an objective part to be photographed, exposure compensation switches 9f are used. Also, in a case of a special photography which cannot be set by the aforesaid operation switches, a mode change-over switch 9g is operated to shift the operation to the manual mode. Then, the quantity of flash light is set by operating switches 9h for setting a flash light quantity. On the assumption that the photography is performed in a dark room, the displays of the part to be photographed and system of photographing are provided with a back illumination together with all the operating switches being of an illuminated type. The information which has been set is indicated by LED.

Also, if a set information is displayed within the field of view of the microscope, its confirmation becomes easier to enable a photographer to notice a mistake, if any, in conducting the photographing.

FIG. 3 is a block diagram showing the arrangement of a CPU 11 for controlling the exposure calculation, the display, and the quantity of flash light. The CPU 11 and a flash light quantity control circuit 12 are arranged in the program exposure control apparatus 4.

The CPU 11 receives magnification information from the variable power mechanism 3 and information regarding the type of camera and film speed from the mounted photographing unit 2. Further, the CPU 11 receives signals regarding the part to be photographed, the exposure compensation for the system of photographing, and others designated through the operation panel 10 as shown in FIG. 2 to perform the LED displays of the operating units and at the same time, to calculate a flash light quantity suited for the current photographing.

The calculation of the flash light quantity is effected on the basis of the sum of each of the coefficients given to the respective exposure elements as follows:

a coefficient of flash light quantity=a variable power coefficient+film coefficient+coefficient of the part to be photographed+coefficient of photographing system+exposure compensation coefficient.

These coefficients are registered in a memory 13 arranged in the exposure control apparatus 4 in advance, and the CPU 11 fetches them as required. The CPU 11 outputs control signals to the flash light quantity control circuit 12 on the basis of the calculated flash light quantity. The flash light quantity control circuit 12 performs controls to select an electrolytic capacitor required for the flash light quantity suited for the photographing unit currently mounted among a plurality of flash light emission electrolytic capacitors to cause the flash light source 6 to perform its light emission on the basis of the control signal from the CPU 11.

The 35 mm photographing unit 2 can be replaced with an instant photographing unit 7, electronic still photographing unit 8, or other unit. Information regarding the photographing unit currently in operation is also output to the program exposure control apparatus 4 so that an optimal flash light quantity can be determined.

In the present embodiment, in calculating an optimal flash light quantity, an actual measurement of the slit width is not performed. For example, when photographing is performed against a lens which is opaquely contaminated, the slit width is estimated to be slightly wider if the retro illumination is applied to this particular photographing, or the slit width is estimated to be narrower if a cross-sectional method, that is, SLIT (a microtonomy image by slitting) is applied. The calculation of an optimal light quantity in response to the slit width thus estimated enables the omission of any complicated mechanism for the detection of slit widths. It suffices if these estimated slit widths are given in advance as parameters. In this respect, it may be possible to provide a slit width detection mechanism for setting the coefficient of the flash light quantity by fetching such an information.

According to an example shown in FIG. 2, one switch is arranged for each of the part to be photographed thereby to select the system of photographing. However, if switches are provided for all the photographing systems, the operativity is further enhanced.

As set forth above, according to the present invention, the part to be photographed and system of photographing are set on the basis of predetermined combinations. Thus, there is an advantage that an optimal exposure can be determined easily for the photographing unit and that any complicated slit width detection mechansim can be omitted.

What is claimed is:

1. A slit lamp microscope having a photographing apparatus for photographing an eye to be examined selectively using a plurality of systems of photographing, and comprising:
    an illumination optical system for illuminating the eye to be examined;
    an observation optical system for observing the eye to be examined under illumination by said illumination optical system;
    a selection switch for selecting a part of the eye to be examined;
    a display for indicating a plurality of systems of photographing suitable for photographing said part of the eye;
    an operation switch which can be operated for selecting one of said plurality of systems of photographing and causing said display to indicate the selected photographing system; and
    exposure value calculation means for calculating an exposure value for said photographing apparatus based on the system of photographing selected by said operation switch.

2. A slit lamp microscope according to claim 1, wherein said display includes a portion for selectively displaying a plurality of speeds of film which can be used in the photographing apparatus.

3. A slit lamp microscope having a photographing apparatus for photographing an eye to be examined selectively using a plurality of systems of photographing, and comprising:
    an illumination optical system for illuminating the eye to be examined;
    an observation optical system for observing the eye to be examined under illumination by said illumination optical system;
    selection means for selecting among parts of the eye to be examined;
    display means for indicating a plurality of systems of photographing suitable for photographing of at least one part of the eye selectable by said selection means;
    operation means for selecting among said plurality of systems of photographing and causing said display means to indicate the selected photographing system;
    exposure control means for controlling an exposure amount of said photographing apparatus at a time of photographing by said photographing apparatus of said one part of the eye to be examined; and
    exposure value calculation means for calculating an exposure value for said photographing apparatus based on the system of photographing selected by said operation means;
    said exposure control means controlling said exposure amount of said photographing apparatus based on the exposure value calculated by said exposure value calculation means.

4. A slit lamp microscope according to claim 3, wherein said illumination optical system is provided with a flash light source, and wherein said exposure control means controls a quantity of light emitted by said flash light source.

5. A slit lamp microscope according to claim 3, wherein said display includes a portion for selectively displaying a plurality of speeds of film which can be used in the photographing apparatus.

6. A slit lamp microscope according to claim 3, wherein said exposure value calculation means includes:

memory means which stores coefficients representing each of said plurality of systems of photographing and said one part of the eye to be examined; and output means for reading from said memory means and outputting the coefficient corresponding to said one part of the eye to be examined and the coefficient corresponding to the system of photographing selected by said operation means; and wherein said exposure value calculation means calculates said exposure value based on each of said coefficients output from said output means.

7. A slit lamp microscope having a photographing apparatus for photographing an eye to be examined selectively using a plurality of systems of photographing, and comprising:

an illumination optical system for illuminating the eye to be examined;

an observation optical system for observing the eye to be examined under illumination by said illumination optical system;

selection means for selecting among parts of the eye to be examined;

display means for indicating, for each of a plurality of said parts of the eye selectable by said selection means, a corresponding plurality of photographing systems suitable for photographing that part of the eye;

operation means for selecting among the respective photographing systems corresponding to each of said plurality of parts of the eye to be examined, and for causing said display means to indicate the selected photographing system for the selected part of the eye to be examined; and exposure value calculation means for calculating an exposure value for said photographing apparatus based on the selected part of the eye to be examined and the selected system of photographing.

8. A slit lamp microscope according to claim 7, further comprising exposure control means for controlling said exposure amount of said photographing apparatus based on the exposure value calculated by said exposure value calculation means.

9. A slit lamp microscope according to claim 8, wherein said illumination optical system is provided with a flash light source, and wherein said exposure control means controls a quantity of light emitted by said flash light source.

10. A slit lamp microscope according to claim 8, wherein said display includes a portion for displaying a plurality of speeds of film which can be used in the photographing apparatus.

11. A slit lamp microscope according to claim 8, wherein said exposure value calculation means includes:

memory means which stores coefficients representing each of said plurality of parts of the eye to be examined and each of the systems of photographing corresponding thereto; and output means for reading from said memory means and outputting the coefficients corresponding to selected part of the eye to be examined and the selected system of photographing; and wherein said exposure value calculation means calculates said exposure value based on the coefficients output from said output means.

* * * * *